United States Patent
Lee et al.

(10) Patent No.: US 9,380,954 B2
(45) Date of Patent: Jul. 5, 2016

(54) METHOD FOR PHYSIOLOGICAL SIGNAL ANALYSIS AND ITS SYSTEM AND COMPUTER PROGRAM PRODUCT STORING PHYSIOLOGICAL SIGNAL ANALYSIS PROGRAM

(71) Applicant: National Cheng Kung University, Tainan (TW)

(72) Inventors: Shuenn-Yuh Lee, Tainan (TW); Shih-Yu Chang Chien, Kaohsiung (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 0 days.

(21) Appl. No.: 14/642,665

(22) Filed: Mar. 9, 2015

(65) Prior Publication Data

US 2015/0359450 A1    Dec. 17, 2015

(30) Foreign Application Priority Data

Jun. 11, 2014  (TW) .............................. 103120259 A (51) Int. Cl.
    *A61B 5/04* (2006.01)
    *A61B 5/00* (2006.01)
    *A61B 5/0476* (2006.01)
    *A61B 5/0432* (2006.01)
    *A61B 5/0488* (2006.01)
    *A61B 5/0456* (2006.01)
    *G06F 19/00* (2011.01)

(52) U.S. Cl.
    CPC ........... *A61B 5/04017* (2013.01); *A61B 5/0432* (2013.01); *A61B 5/0476* (2013.01); *A61B 5/0488* (2013.01); *A61B 5/7475* (2013.01); *A61B 5/0456* (2013.01); *A61B 5/726* (2013.01); *G06F 19/30* (2013.01)

(58) Field of Classification Search
    CPC ........... A61B 5/04012; A61B 5/04014; A61B 5/04017; A61B 5/7264; A61B 5/7267; A61B 5/7271; A61B 5/72; A61B 5/7275; A61B 5/7282; A61B 5/7235; A61B 5/7225; A61B 5/7253; A61B 5/04001
    See application file for complete search history.

(56) References Cited

U.S. PATENT DOCUMENTS

2010/0211125 A1* 8/2010 Johnson ............. A61B 5/02405 607/4

* cited by examiner

*Primary Examiner* — Robert N Wieland
(74) *Attorney, Agent, or Firm* — Chun-Ming Shih (57) ABSTRACT

A method for physiological signal analysis and its system and a computer program product storing a physiological signal analysis program are provided. Physiological signals of a subject are collected for a user to provide a detection opinion for the physiological signals in order to generate syndrome recognition parameters and syndrome weight parameters such that the collected physiological signals are analyzed and determined. The invention performs detection determination by means of combining the physiological signals of the subject and referencing to an analysis opinion from the user. Therefore, an output detection result may be believed by both doctors and patients with effectively improved accuracy of analysis result to improve the efficiency of the user in diagnosis and treatment.

17 Claims, 4 Drawing Sheets

METHOD FOR PHYSIOLOGICAL SIGNAL ANALYSIS AND ITS SYSTEM AND COMPUTER PROGRAM PRODUCT STORING PHYSIOLOGICAL SIGNAL ANALYSIS PROGRAM

CROSS-REFERENCE TO RELATED APPLICATIONS

This application claims the priority of Republic of China Patent Application No. 103120259 filed on Jun. 11, 2014, in the State Intellectual Property Office of the R.O.C., the disclosure of which is incorporated herein by reference.

BACKGROUND OF THE INVENTION

1. Field of the Invention

The invention relates to a physiological signal analysis technology, particularly to a physiological signal analysis system for analysis by combining physiological data of a subject and user opinion and the method thereof and a computer program product storing physiological signal analysis program.

2. Descriptions of the Related Art

According to the worldwide top 10 death causes published by WHO (World Health Organization) in 2011, the death of people due to cardiovascular diseases plays the major role. Most of such diseases need long term monitoring and treatment. However, patients cannot stay in hospital to accept monitoring and treatment for long time because of realistic conditions and limited resources, but can only be cared with outpatient service. However, abnormal physiological signal response due to such diseases occurs only in short attack. Moreover, such irregular generation of abnormal physiological signal occurs usually in daily life of patients. Therefore, abnormal conditions of patients occurred in daily life cannot be monitored effectively and in real time for traditional outpatient service, such that doctors cannot diagnose diseases suffered by patients accurately as patients see doctors in most case.

In view of above issues, the industry has promoted health care systems integrated with communication and physiological signal monitoring and retrieval features one after another. In a wireless transmission physiological detection system, for example, the physiological signals of patients, such as brain waves and electrocardiographic signals are retrieved by an analog front-end system, followed by transmission to a receiving end through wireless transmission method for process in order to monitor and analyze physiological signal conditions of patients, such that patients do not have to stay in hospital while medical service and support can still be taken. However, lots of unnecessary data would be generated because such remote medical system needs long term monitoring. In addition to consume storage space, these data can also confuse doctors in reading.

Furthermore, most of known physiological signal monitoring technologies are implemented by software. These technologies can only be operated on computers finally because limits for hardware implementation are not considered. Specific algorithms are used for these technologies if hardware is implemented, which results in relatively high complexity. Although its effectiveness is proved from investigation data, it violates human determination used by doctors. As such, doctors usually cannot accept the diagnosis result calculated by such systems without doubt at last.

SUMMARY OF THE INVENTION

In view of various issues of above prior arts, one objective of the invention is to provide a physiological signal analysis method and the system thereof, and a computer program product storing physiological signal analysis program. Physiological data of a subject and opinion of a user are combined for analysis to reduce system complexity and improve accuracy of analysis result effectively. The software and hardware developed in the invention would be capable of artificial intelligence for real time syndrome analysis and screening, such that analyzing and determination result can be accepted further by both doctors and patients.

Another objective of the invention is to provide a physiological signal analysis method and the system thereof, and a computer program product storing physiological signal analysis program, in order to reduce inputs of unnecessary data during monitoring. It is useful for the user to obtain effective daily physiological signal monitoring data as the subject returns to clinics, such that the difficulty of data reading is reduced to reduce work load of the user effectively.

To achieve above object and other object, the invention provides a physiological signal analysis method, the method including steps of: collecting physiological signal from a subject; retrieving characteristic values from said physiological signal for detection of a predetermined waveform and output of a detection result; allowing user to enter syndrome evaluation data according to said detection result; generating syndrome recognition parameters and syndrome weight parameters according to said entered syndrome evaluation data for saving; and analyzing the physiological signal collected from the subject according to the saved syndrome recognition parameters, and outputting a determination result.

Preferably, said physiological signal includes EEG, ECoG, EKG, EMG or ECG physiological signal.

Preferably, the analysis and detection steps of said predetermined waveform includes steps of: defining peak detection intervals of the physiological signal, and setting threshold parameters of input data in said peak detection intervals, said threshold parameters being used for excluding unnecessary sampling points in said peak detection intervals; receiving said collected physiological signal input data until the collected physiological signal input data is determined to satisfy said set threshold of the input data in the peak detection intervals; obtaining peak data of the physiological signal in each of said peak detection intervals; and comparing waveform presence time corresponding to the peak data of two of the adjacent peak detection intervals to determine whether or not said two sets of peak data belong to the same physiological signal, and updating said set threshold parameters of the input data in the peak detection intervals according to said determination result, and obtaining peak presence time of said physiological signal.

Preferably, the steps of outputting the determination result output from the analysis for the physiological signal collected from the subject according to the saved syndrome recognition parameters and syndrome weight parameters include steps of: collecting the physiological signal from the subject in one peak detection interval according to said defined peak detection intervals, and executing wavelet transform process for the physiological signal collected in said peak detection intervals to generate wavelet coefficients; obtaining the peak presence time in said peak detection interval; dividing the peak detection interval in which said peak presence time is obtained into a plurality of small intervals, calculating a sum of differences between two curves of the wavelet coefficients and said saved syndrome recognition parameters in each of the small intervals; and grading each of said divided small intervals according to the calculated sum of the differences between said two curves, wherein process of said grading is based on syndrome grades corresponding to said syndrome recognition parameters, wherein said syndrome grade is one of the aforementioned syndrome weight parameters, and the syndrome grades of each of the small intervals are summed for analysis and output of said determination result.

Preferably, a small one calculated sum of the differences between the two curves of the wavelet coefficients in the small intervals and said saved syndrome recognition parameters indicates that the physiological signal from said subject is close to said saved syndrome recognition parameters, such that said syndrome grades can be graded.

Preferably, the steps of outputting the determination result output from the analysis for the physiological signal collected from the subject further include steps of: after the syndrome grades of said small intervals being graded because of the small sum of the differences between the two curves of the calculated wavelet coefficients in the small intervals and said saved syndrome recognition parameters, summing the syndrome grades of said syndrome recognition parameters of each of the small intervals, and determining the syndrome indicated by said peak detection intervals according to high syndrome grades corresponding to said syndrome recognition parameters.

Preferably, before summing the syndrome grades of said syndrome recognition parameters of each of the small intervals further including steps of: setting parameter values for recording grading number, wherein said grading number is one of the aforementioned syndrome weight parameters, recording said grading number as the calculated sum of the differences between the two curves of the wavelet coefficients in the small intervals and said saved syndrome recognition parameters is small, and performing the step of summing the syndrome grades of each of said syndrome recognition parameters for each of the small intervals as said grading number reaches a predetermined value.

Preferably, further including steps of: allowing the user to modify the entered syndrome evaluation data based on said determination result in order to optimize said saved syndrome recognition parameters and syndrome weight parameters.

Furthermore, the invention further provides a computer program product for storing physiological signal analysis program, wherein the steps of the physiological signal analysis method aforementioned are completed after said computer program product has said program loaded and executed.

Moreover, the invention further provides a physiological signal analysis system for user to determine syndrome by a physiological signal from a subject, the system including: a physiological signal detection module for retrieving characteristic values of the physiological signal collected from the subject in order for detection of a predetermined waveform and output of the detection result; a syndrome evaluation module for the user to determine the syndrome according to the detection result output by said physiological signal detection module, and to enter corresponding syndrome evaluation data for generating syndrome recognition parameters and syndrome weight parameters according to said entered syndrome evaluation data; and a determination module for analyzing the detection result output by said physiological signal detection module according to the syndrome recognition parameters and syndrome weight parameters generated by said syndrome evaluation module, and for outputting a determination result.

Preferably, said physiological signal includes EEG, ECoG, EKG, EMG or ECG physiological signal.

Preferably, said physiological signal detection module includes: a digital filter unit for filtering out noise in said collected physiological signal, and outputting a signal of a frequency band occupied by said retrieved physiological signal; a wavelet transform unit for executing wavelet transform process for the signal output by said digital filter unit to generate wavelet coefficients in order to retrieve characteristic values in said physiological signal, and saving said generated wavelet coefficients in a storage unit; and a peak detection unit for performing waveform analysis and detection for the wavelet coefficients in said storage unit to obtain peak presence time of said physiological signal, and outputting said detection result.

Preferably, said peak detection unit predefines the peak detection intervals of the physiological signal, and sets threshold parameters of input data in said peak detection intervals, said threshold parameters being used to exclude unnecessary sampling points in said peak detection intervals, and to receive the input data of said collected physiological signal until the input data of the collected physiological signal is determined to satisfy threshold of the input data in said set peak detection intervals; obtains peak data of the physiological signal in each of said peak detection intervals; compares waveform presence time corresponding to the peak data of two of the adjacent peak detection intervals in order to determine whether or not said two peak data are both belong to the same physiological signal, and update the threshold parameters of the input data in said set peak detection intervals according to said determination result, and obtain the peak presence time of said physiological signal.

Preferably, the aforementioned system further including: a syndrome evaluation storage module for saving the syndrome recognition parameters generated by said syndrome evaluation module, said determination module collecting the physiological signal of the subject in one peak detection interval according to said defined peak detection interval, and obtaining the peak presence time in said peak detection interval, and the wavelet coefficients corresponding to the physiological signal in said peak detection interval, dividing the peak detection interval of said obtained peak presence time into a plurality of small intervals, calculating sum of differences between two curves for the wavelet coefficients in each of the small intervals and said saved syndrome recognition parameters, grading each of said divided small intervals according to the sum of the differences between said calculated two curves, wherein said grading is processed according to syndrome grades corresponding to said syndrome recognition parameters, wherein said syndrome grade is one of the aforementioned syndrome weight parameters, and the syndrome grades of each of the small intervals are summed for analysis to result in and output said determination result.

Preferably, a small one calculated sum of the differences between the two curves of the wavelet coefficients in the small intervals and said saved syndrome recognition parameters indicates that the physiological signal from said subject is close to said saved syndrome recognition parameters, such that said syndrome grades can be graded.

Preferably, after the syndrome grades of said small intervals being graded because of the small sum of the differences between the two curves of the calculated wavelet coefficients in the small intervals and said saved syndrome recognition parameters by the determination module, summing the syndrome grades of said syndrome recognition parameters of each of the small intervals, and determining the syndrome indicated by said peak detection intervals according to high syndrome grades corresponding to said syndrome recognition parameters.

Preferably, said determination module further sets parameter values to record grading number, wherein said grading number is one of the aforementioned syndrome weight parameters, said grading number is recorded as the sum of the differences between the two curves for the calculated wavelet coefficients in the small intervals and the saved syndrome recognition parameters is small, and the syndrome grades of each of the syndrome recognition parameters for each of the small intervals are summed as said grading number reaches a predetermined value, such that the syndrome belonging to said peak detection interval is determined according to the high syndrome grades corresponding to the syndrome recognition parameters.

Preferably, said digital filter unit is low pass filter, high pass filter, band pass filter, notch filter, or the combination thereof.

Preferably, the aforementioned system further including: a syndrome evaluation storage module, and said syndrome evaluation module including: a wavelet inverse transform unit for executing wavelet inverse transform process for the wavelet coefficients output by said wavelet transform unit in order to restore an original physiological signal thereof; a syndrome evaluation unit for the user to determine syndrome from the detection result output by said peak detection unit, and to enter the corresponding syndrome evaluation data; and a conversion unit for generating the syndrome recognition parameters and syndrome weight parameters according to the syndrome evaluation data input from said syndrome evaluation unit, and for saving thereof in said syndrome evaluation storage module.

Compared to conventional technologies, the physiological signal analysis method and the system thereof and the computer program product storing physiological signal analysis program, which combine opinions of users (such as medical personnel) and physiological data of subjects for analysis and determination, can reduce error rate of analysis and determination effectively. Moreover, artificial intelligence and machine learning are introduced in the design of software and hardware, such that the analysis result can be further accepted by both doctors and patients. Thus, its practical value is improved. In addition, the invention can also reduce inputs of unnecessary data, such that system operation load can be reduced, hardware cost can be lowered, and complexity of diagnosis work of doctors can be simplified.

DETAILED DESCRIPTION OF THE PREFERRED EMBODIMENT

Embodiments of the present invention will now be described in detail with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the invention to those skilled in the art. In the drawings, the shapes and dimensions of elements may be exaggerated for clarity, and the same reference numerals will be used throughout to designate the same or like components.

Figure 1:
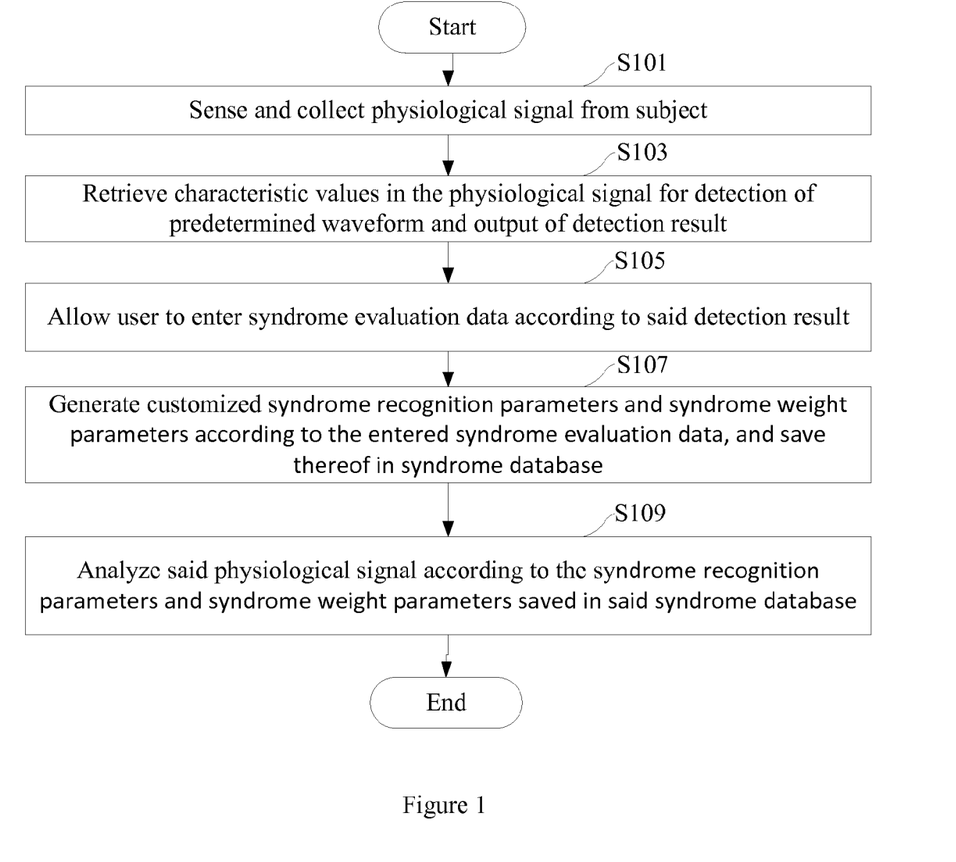
FIG. 1 is an operation flowchart illustrating the physiological signal analysis method according to the invention.

Refer to FIG. 1, which is an operation flowchart showing the physiological signal analysis method according to the invention. As shown in the figure, step S101 is executed at first to sense and collect a physiological signal of a subject. In the example, the sensed physiological signal includes: EEG, ECoG, EKG, EMG or ECG physiological signal. Next, step S103 is performed.

In step S103, characteristic values in said physiological signal are retrieved for detection of a predetermined waveform and output of a detection result. Specifically, the invention utilizes a predetermined algorithm (for example, Haar wavelet transform) at first to perform wavelet transform for the physiological signal from said subject and to retrieve the characteristic values thereof, and it is saved in a storage unit, such as memory or register, followed by using transformed wavelet coefficients to perform peak detection in order to find out every physiological signal peak. Once peaks are found out, a fixed length wavelet analysis value is extracted from said storage unit, and said wavelet analysis value and said sensed physiological signal are used as the detection result for output (as illustrated below in FIG. 2). Next step S105 is performed.

In step S105, the user is allowed to perform diagnosis based on said output detection result, and enter syndrome evaluation data. In the example, said output wavelet analysis value contains a corresponding note time point. According to the note time point corresponding to said wavelet analysis value, the user enters the associated syndrome and the detect interval range necessary for diagnosis as the basis for subsequent generation of syndrome recognition parameters and syndrome weight parameters. Then, step S107 is performed.

In step S107, based on the syndrome evaluation data entered by the user, customized syndrome recognition parameters and syndrome weight parameters are generated, which are saved in a syndrome evaluation storage module after above parameter data are identified by the user. Next, step S109 is performed.

In step S109, according to the syndrome recognition parameters and syndrome weight parameters saved in said syndrome evaluation storage module, the received physiological signal is analyzed to determine the syndrome corresponding to said physiological signal, and the corresponding determination result is output for the user to identify said determination result. Functions of the aforementioned syndrome recognition parameters and syndrome weight parameters will be illustrated in FIG. 3 in detail.

In the case of electrocardiographic detection, the user may observe the physiological signal from the subject through a display interface. Moreover, as abnormal heartbeat signal occurs, related syndrome note may be added and the weight proportion thereof is set for said physiological signal. Accordingly, the invention will generate the syndrome recognition parameters and syndrome weight parameters corresponding to said abnormal heartbeat signal. Furthermore, as the next data is entered, the invention performs syndrome determination with said existing syndrome recognition parameters and syndrome weight parameters. If the user agrees to said determination result, only the identified entering has to be performed. On the contrary, the user modifies said related syndrome recognition parameters or syndrome weight parameters. For example, the user may modify the grading number (TopN) as illustrated in the following FIG. 3 until the output determination result meets the medical opinion of the user. Such process is the secondary optimization process for the syndrome recognition parameters and syndrome weight parameters. Thereby, the determination error rate of the detection result is reduced, such that the reliability of the user for physiological signal detection and analysis instruments in actual operation process is improved to aid the user in improving the efficiency of diagnosis and treatment works effectively.

Figure 2:
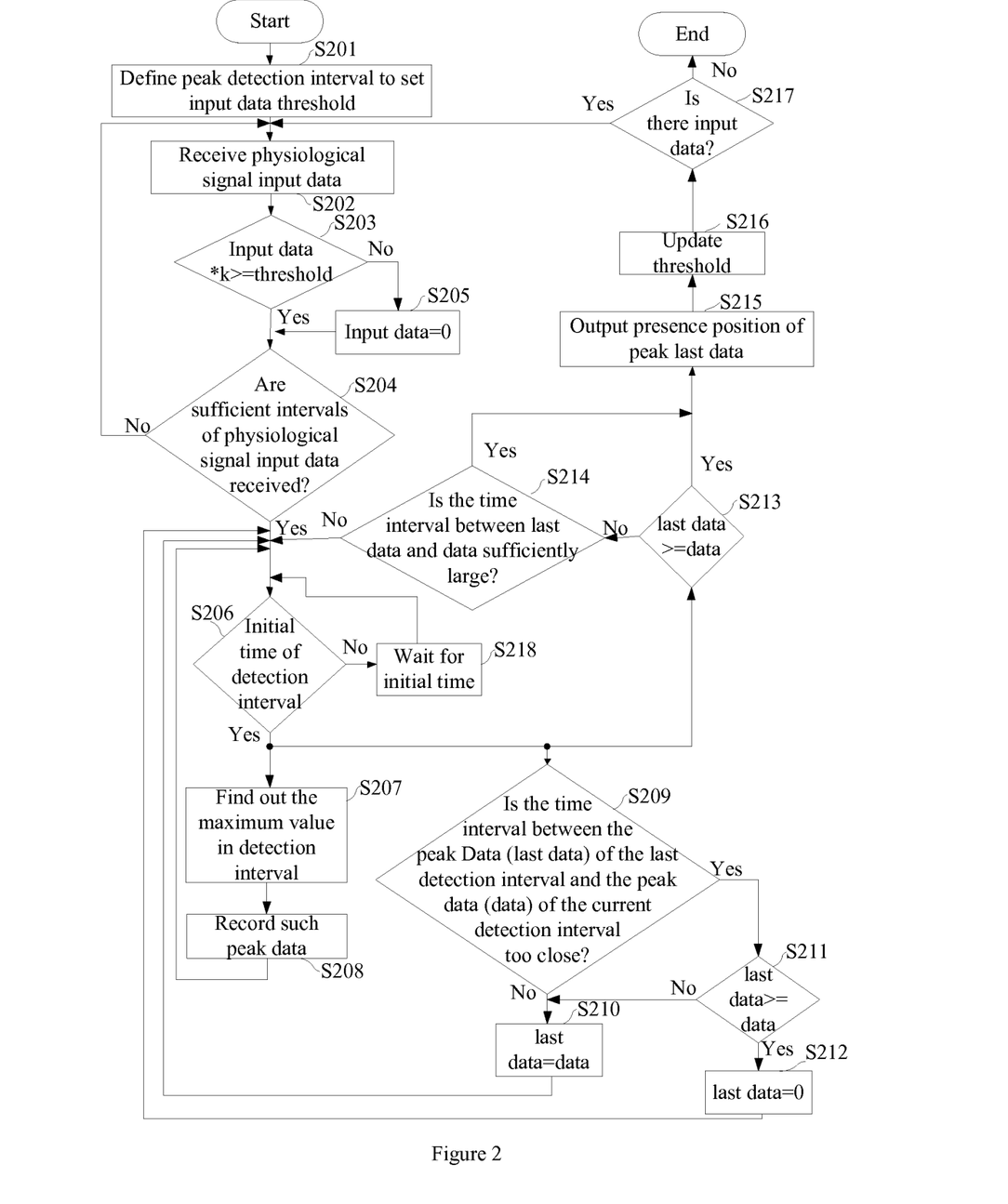
FIG. 2 is a specific operation flowchart showing the detection step for a predetermined waveform in step S103 of the physiological signal analysis method disclosed in FIG. 1.

FIG. 2 is a specific operation flowchart showing the detection step for a predetermined waveform in step S103 of the aforementioned physiological signal analysis method. The heartbeat detection, for example, is used to illustrate the detection flow of the predetermined waveform according to the invention specifically below.

At first, step S201 is performed by defining peak detection intervals of the physiological signal, and setting threshold parameters (threshold) of input data in said peak detection intervals. With respect to the aforementioned electrocardiographic detection, for example, the peak detection interval here indicates heartbeat detection interval. There are 128 sampling points based on the calculation of 480 Hz sampling frequency for human heartbeat, which upper bound of speed is 220 bpm. Thus, the invention defines said peak detection interval as 128 sampling points. None or only one heartbeat would occur in such interval, in which there would be no occurrence of two heartbeats. As such, only the maximum value has to be determined for each peak detection interval. Furthermore, frequency and sampling points may be adjusted according to patient symptom and user requirement to detect fatal heartbeat variation, such as a heartbeat rate up to 400 bpm. In addition, since the input data are entered in order and are in real time, the next step is conducted only after one interval of data has been collected. Thus, the invention allows for setting threshold parameters for a set of input data, such that some sampling points that have no way to be heartbeat presence time are eliminated in order to reduce the data necessary for computation, and thereby, to reduce operation load of the physiological signal analysis system while simplify the complexity of data reading for the user. Then, step S202 is performed.

In step S202, physiological signal input data (input_data) is received, followed by proceeding to step S203.

In step S203, the collected physiological signal input data is determine to see whether the threshold of the input data in said set peak detection interval is satisfied (i.e., input_data*k>=threshold). Step S204 is proceeded if it is satisfied, or otherwise, step S205 is proceeded.

In step S204, it determines whether or not sufficient physiological signal input data for performing one peak detection interval is received, and proceeds to step S206 if the determination results in Yes, or otherwise, step S202 is executed again to input data continuously if the determination results in No.

In step S205, if the input data is smaller than said set threshold, then the input data is replaced with 0, i.e., input_data=0, and it proceeds to step S204.

In step S206, it determines whether or not it is at initial time of the peak detection interval. In this step, there may be complete computation time for a complete detection interval and synchronous output effect may be achieved in subsequent waveform recognition. If it determines that it is not at the initial time of the detect interval, it proceeds to step S218. Once the initial time of the peak detection interval is reached, step S206 is executed again. In the contrary, if it determines that it is at the initial time of the detect interval, it may proceeds optionally to step S207, S209 or S213. It is noted that there is no order in executing step S207, S209 or S213. These steps may also be executed simultaneously, wherein step S207 finds out peak data in said peak detection interval, step S209 determines whether or not two sets of peak data in two adjacent peak detection intervals are for the same heartbeat, and step S213 outputs real heartbeat time.

In step S207, the maximum value in said peak detection interval is searched. In this step, the peak data of the physiological signal in each peak detection interval is obtained, followed by proceeding to step S208.

In step S208, said peak data is recorded if said input data that is found out is the maximum value in said peak detection interval, and is saved in a storage unit, such as register, and it returns to execute step S206.

In step S209, the waveform presence time corresponding to the peak data in two adjacent peak detection intervals are compared. In this example, the peak data in the last peak detection interval is recorded as last_data, and the peak data in the current peak detection interval is recorded as data. This step determines whether or not the time interval between last_data and data is too close. It proceeds to step S211 if Yes is resulted. If No is resulted, it determines that the time interval between the peak data in the last peak detection interval and the peak data in the current peak detection interval is sufficiently large, which indicates that the peak data in the current peak detection interval might be heartbeat, and proceeds to step S210.

In step S210, the peak data of the last peak detection interval is overridden by the current peak detection interval, i.e., last_data=data, and it returns to execute step S206.

In step S211, if the time interval between the peak data in the last peak detection interval and the peak data in the current peak detection interval is too close from analysis, then it keeps on determining whether or not the peak data in the last peak detection interval is larger than or equal to the peak data in the current peak detection interval (i.e., last_data>=data). If it results in Yes, then it determines that the time interval between the two pieces of peak data is too close, and the peak data in the last peak detection interval, last_data, is relatively large so that it proceeds to step S212. Otherwise, it determines that the time interval between the two pieces of peak data is too close, and the peak data in the last peak detection interval (last_data) is relatively small so that it proceeds to step S210 for overriding the peak data (last_data) of the last peak detection interval with peak data (data) of the current peak detection interval.

In step S212, it indicates that if the peak data (last_data) saved in the last peak detection interval is real heartbeat, then the register for saving last_data is cleared after the peak data is output, that is, last_data=0, and it returns and executes step S206.

In step S213, as mentioned above, it outputs the time at which the real heartbeat is output. Since the real heartbeat value has been saved in the register of last_data through the determination in step S209, in order to improve the accuracy of detection data, the value data of last_data and data will be compared synchronously, that is, last_data>=data is determined. It proceeds to step S214 if No is resulted, or it proceeds to step S215 if Yes is resulted.

In step S214, it determines whether or not the time interval between last_data and data is sufficiently large. It proceeds to step S215 if Yes is resulted, or it returns and executes step S206 if No is resulted.

In step S215, the presence time of the peak last_data is output, that is, the presence time of the real heartbeat is output, and it proceeds to step S216.

In step S216, said threshold is updated with reference to the latest peak data. In normal condition, the value of the real heartbeat must be larger than a certain predetermined value, which would influence detection accuracy. Therefore, said threshold has to be updated in order to find out said predetermined value. In this example, the current threshold is added with the mean of real heartbeat values, such that said threshold approximates to said predetermined value indefinitely, following by proceeding to step S217.

In step S217, it determines whether or not there is subsequent data input. It ends the step if it determines that there is no data input, or it returns and executes step S202 if it determines that there is subsequent data input.

Figure 3:
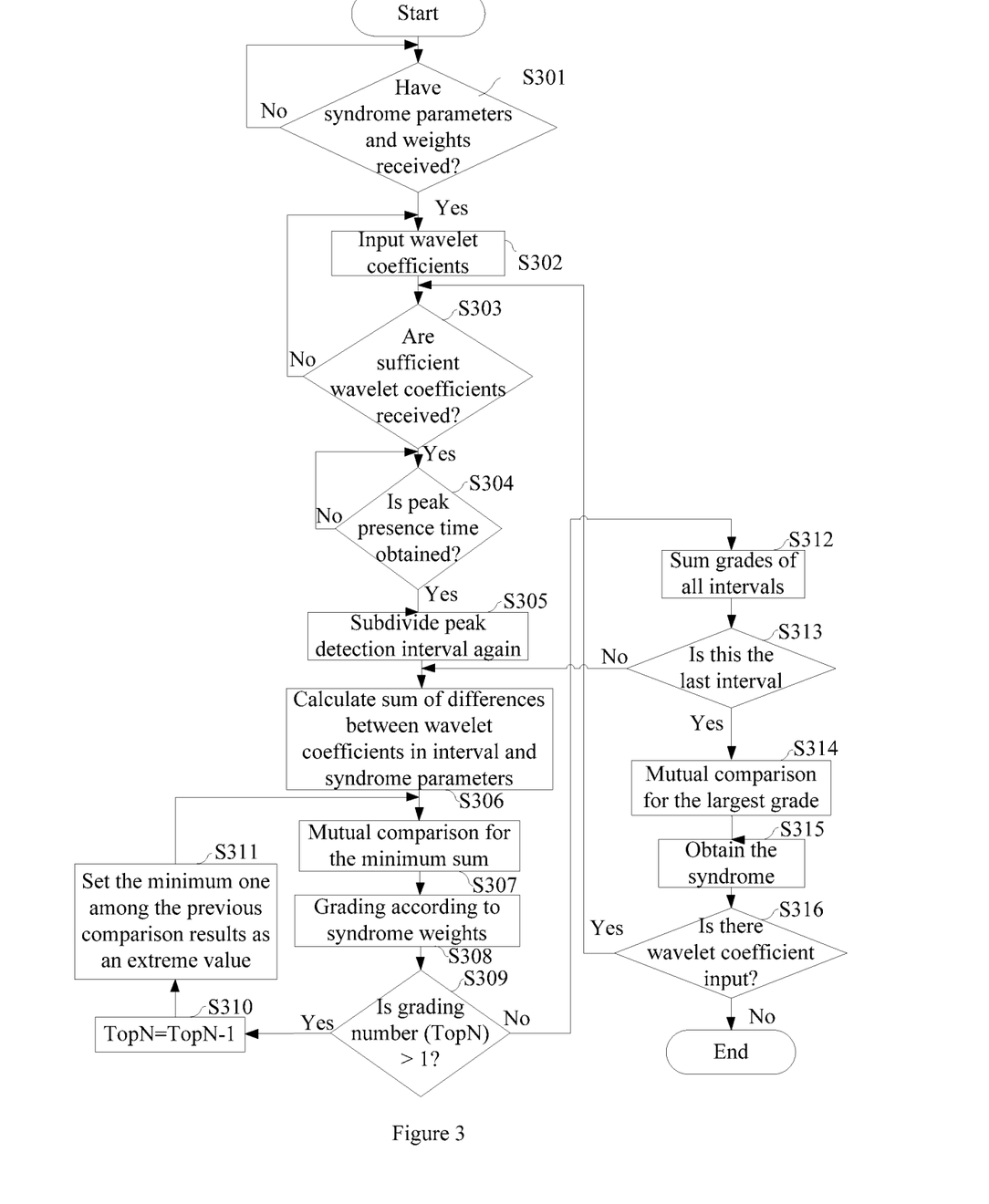
FIG. 3 is a specific operation flowchart showing the syndrome recognition step for step S109 in the physiological signal analysis method disclosed in FIG. 1.

Then, refer to FIG. 3, which is a specific operation flowchart showing the syndrome analysis step in step S109 in the physiological signal analysis method shown in FIG. 1. As above, heartbeat detection, for example, is used to illustrate specifically the process flow of the physiological signal analysis method of the invention for syndrome recognition.

At first, step S301 is performed to update the syndrome recognition parameter data and syndrome weight parameter data in said syndrome evaluation storage module, and to determine whether or not said syndrome recognition parameters and syndrome weight parameters have been received. It proceeds to step S302 if Yes is resulted, or it repeats the step S301 if No is resulted.

In step S302, it collects the physiological signal from the subject in one peak detection interval according to said defined peak detection interval, and executes wavelet transform process for the physiological signal collected in said peak detection interval to generate wavelet coefficients, followed by proceeding to step S303.

In step S303, it determines whether the wavelet coefficients sufficient to perform one peak detection interval have been received. It proceeds to step S304 if Yes is resulted, or it returns to step S302 to keep on receiving wavelet coefficients.

In step S304, the peak presence time in said peak detection interval is detected to detect the heartbeat presence time. It proceeds to step S305 if the peak presence time in the peak detection interval is detected, or it repeats to execute step S304 if no peak presence time is detected.

In step S305, the peak detection interval with said peak presence time detected is divided into several small intervals. In this example, in order to increase recognition accuracy while reduce hardware cost, the invention subdivides one peak detection interval (as the aforementioned 128 sampling points) into 4 small intervals (for example, 32 sampling points), and proceeds to step S306.

In step S306, the sum of the differences between two curves of the wavelet coefficients in one small interval and the syndrome recognition parameters saved in said evaluation storage module is calculated, followed by proceeding to step S307.

In step S307, the sums of differences are compared mutually for the minimum one in order to find out the most similar syndrome, followed by proceeding to step S308.

In step S308, said small intervals are graded according to the syndrome weight parameters saved in said syndrome evaluation storage module, wherein said grading process is based on the syndrome grades corresponding to said syndrome recognition parameters, wherein said syndrome grade may also be one of the aforementioned syndrome weight parameters. In this example, the user may set each small interval (32 sampling points) with a grade from 0 to 15 (syndrome grade), and set the grading number for the same small interval (the grading number is one of the aforementioned syndrome weight parameters), followed by proceeding to step S309.

In step S309, it determines the grading number (TopN)>1 of such small interval. It proceeds to step S310 if the value is larger than 1, or it proceeds to step S312 if the value is not larger than 1. In addition, the execution of steps S309 and S310 may not be necessary for every detection of one piece of peak data. For ECG, for example, the major detection is for R wave. In this step, it mainly detects whether or not heartbeat occurs. As for other waveforms, for example, a particular waveform is detected by simply waiting for such particular waveform. That is, in the steps S309 and S310 illustrated in FIG. 3 of the invention, the result of the predetermined waveform to be detected in FIG. 2 may be used to decide whether or not said grading number (TopN) has to be set (for example, the grading number is set to 1(TopN=1)). Specifically, as shown above, for steps from S209 to S211 in the predetermined waveform detection step shown in FIG. 2, it mainly determines whether the peaks of two adjacent intervals are the same signal. If two peaks are detected now while the two peaks are the same signal, then the flow shown in FIG. 3 has to be executed for only one time.

In step S310, it subtracted the value of the grading number by 1, that is, TopN=TopN−1, followed by proceeding to step S311.

In step S311, it sets the minimum one of the previous comparison results, i.e., the comparison results in step S307, to be an extreme value, in order to avoid repetitive selection, and returns to step S307 for secondary grading process according to the syndrome grades corresponding to said syndrome recognition parameters until the grading number TopN is 1.

In step S312, as it determines that the grading number (TopN) of the small interval is 1, the syndrome grades of all of the small intervals that have been obtained currently (i.e., the step performing grading syndrome grades corresponding to each of said syndrome recognition parameters in the aforementioned step S308) are summed, followed by proceeding to S313.

In step S313, it determines whether or not the currently computed small interval is the last small interval. It proceeds to step S314 if Yes is resulted, or it returns to perform step S306 if the grading for all small intervals have not yet been processed.

In step S314, the syndrome grades corresponding to each of said syndrome recognition parameters are compared with each other. Based on the syndrome recognition parameter with the highest syndrome grade, it proceeds to step S315.

In step S315, said syndrome recognition parameter with the highest grade among said syndrome grades is found out and output for the user to identify said output detection result, followed by proceeding to step S316. In addition, the physiological signal analysis system of the application may further allow the user to modify the entered syndrome evaluation data according to said detection result in order to optimize the syndrome recognition parameters and syndrome weight parameters saved in said syndrome evaluation storage module, such that the accuracy for the diagnosis and treatment of the physiological signal analysis system is improved.

In step S316, it determines whether there is subsequent input of wavelet coefficients. It ends this step if it determines that there is no input of wavelet coefficients, or it returns to and performs step S302 if it determines that there is subsequent input of wavelet coefficients.

The setting for the aforementioned grading number (TopN) is used to perform multiple times of grading. Different syndromes would also have similar waveforms for the same small interval in the same peak detection interval, such that mutual grading competition would occur for different syndromes in the same small interval, and thus the recognition rate would be reduced. Hence, in the invention, if the sum of the differences between the two curves of the input data of the small intervals and said saved syndrome recognition parameters is determined to be the minimum one, said grading number (TopN) is recorded, and 2, 3 or 4 times of grading are rendered for said determined syndrome grades (initial grading) and the determined grading number (TopN). Moreover, the user may save the syndrome weight parameters after the aforementioned waveform recognition process to be the criteria for the next physiological condition analysis of said subject, and to be the comparison criteria for the next determination of progress or degradation of the physiological condition of said subject. Furthermore, syndrome recognition parameters may be updated or added accordingly for subsequent reference sources to be more complete.

Additionally, with respect to applications, the physiological signal analysis method of the invention may be applied to a physiological signal detection and analysis instrument. Said physiological signal detection and analysis instrument executes directly the physiological signal analysis method of the invention as illustrated in FIGS. 1, 2 and 3. That is, the user analyzes physiological signal from said subject through said physiological signal detection and analysis instrument. Therefore, the invention may further provide a computer program product storing physiological signal analysis program. Said computer program product, for example, user end electronic device such as physiological signal detection and analysis instrument, executes various steps as illustrated in FIGS. 1, 2 and 3 by means of said physiological signal analysis program.

In addition, it is noted that in the step S101 shown in FIG. 1, the physiological signal analysis method of the invention may be performed in another user end electronic device for the physiological signal sensing step of the subject. In other words, the aforementioned step S101 in FIG. 1 may be simply the collection of the physiological signal of a subject.

Figure 4:
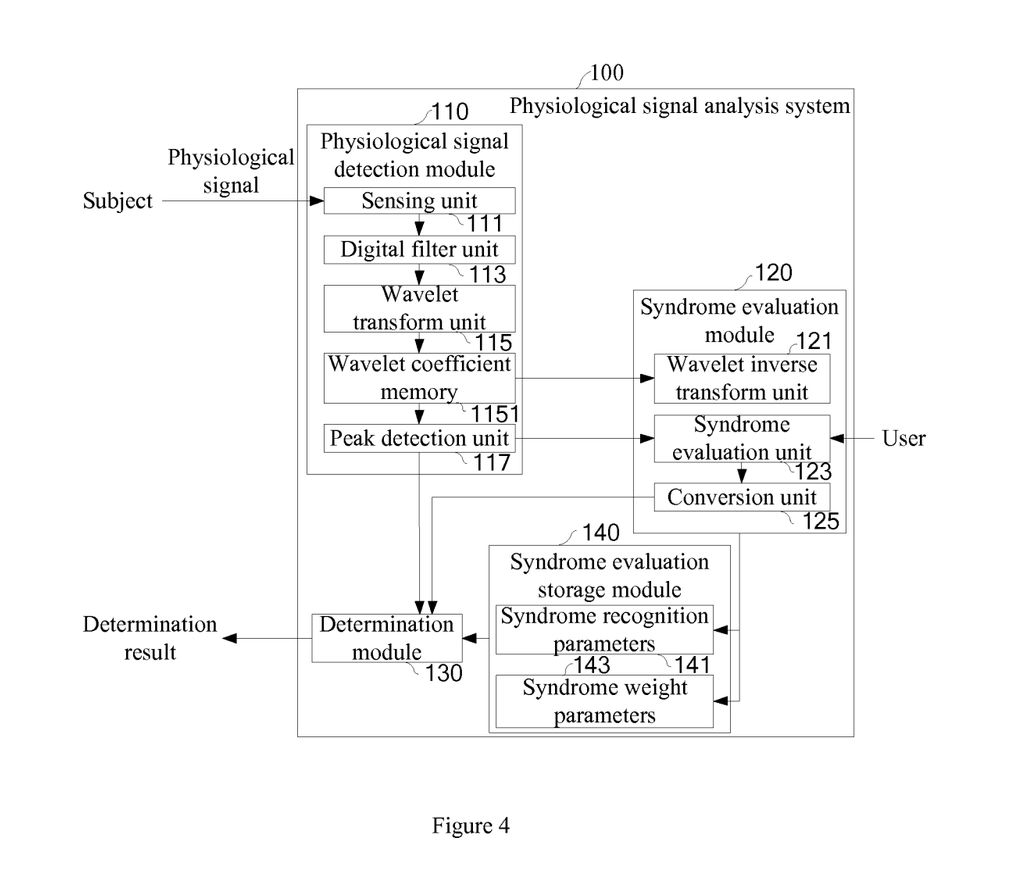
FIG. 4 is a basic system architecture diagram of the physiological signal analysis system according to the invention.

Moreover, refer to FIG. 4. FIG. 4 is a basic system architecture diagram of the physiological signal analysis system according to the invention. The physiological signal analysis system of the invention includes: a physiological signal detection module 110, a syndrome evaluation module 120, a syndrome evaluation storage module 140 and a determination module 130.

The physiological signal detection module 110 is used to sense and collect the physiological signal from the subject, and utilize a predetermined algorithm to retrieve characteristic values from said collected physiological signal for detection of a predetermined waveform and output of said detection result, wherein said physiological signal may be EEG, ECoG, EKG, EMG or ECG physiological signal. In this example, said physiological signal detection module 110 includes: a sensing unit 111, a digital filter unit 113, a wavelet transform unit 115, and a peak detection unit 117. It is noted that, as above, the process of sensing the physiological signal from the subject done by the physiological signal detection module 110 in the physiological signal analysis system of the invention may be executed by another user end electronic device (not shown). In short, the physiological signal detection module 110 of the invention retrieves characteristic values from said collected physiological signal for detection of predetermined waveform. Moreover, in this example, sensing of physiological signal is integrated into the physiological signal detection module 110, but from above, the invention is not limited thereto.

The sensing unit 111 is used to sense and collect the physiological signal from the subject. The digital filter unit 113 is used to filter out noise in the physiological signal sensed by said sensing unit 111, and retrieve the frequency band signal occupied by the physiological signal, wherein said digital filter unit 113 is low pass filter, high pass filter, band pass filter, notch filter or the combination thereof, but the invention is not limited thereto. The wavelet transform unit 115 is used to execute wavelet transform process for the physiological signal output by said digital filter unit 113 to generate wavelet coefficients, in order to retrieve the characteristic values in said physiological signal, and save said generated wavelet coefficients in a wavelet coefficient memory 1151 (but no limited thereto, and can be in storage unit such as register etc.). The peak detection unit 117 utilizes a predetermined algorithm to perform waveform analysis and detection for wavelet coefficients in said wavelet coefficient memory 1151 in order to obtain peak presence time of each physiological signal, and output said detection result.

The syndrome evaluation module 120 is used to allow the user to perform syndrome determination according to the detection result output by said physiological signal detection module 110, and entered corresponding syndrome evaluation data, and to generate customized syndrome recognition parameters 141 and syndrome weight parameters 143 according to said entered syndrome evaluation data and save thereof in the syndrome evaluation storage module 140. In this example, said syndrome evaluation module 120 includes: a wavelet inverse transform unit 121, a syndrome evaluation unit 123 and a conversion unit 125.

The wavelet inverse transform unit 121 executes wavelet inverse transform process for the wavelet coefficients output by said wavelet transform unit 115, restores thereof to the original physiological signal, and outputs thereof on a display interface (not shown) as reference for the user to perform syndrome evaluation. The syndrome evaluation unit 123 is used for the user to determine syndrome from the detection result output by said peak detection unit 117, and to enter the corresponding syndrome evaluation data. The conversion unit 125 is used to generate customized syndrome recognition parameters 141 and syndrome weight parameters 143 according to the syndrome evaluation data input from said syndrome evaluation unit 123, and save thereof in the syndrome evaluation storage module 140, wherein said syndrome evaluation storage module 140 and the aforementioned wavelet coefficient memory 1151 may be SRAM (Static Random Access Memory), DRAM (Dynamic Random Access Memory), EPROM (Electrically Programmed ROM) or any volatile, nonvolatile or other types of memories or storage units, but the invention is not limited thereto.

The determination module 130 is used to analyze the detection result output by the physiological signal detection module 110 according to the syndrome recognition parameters 141 and syndrome weight parameters 143 saved in said syndrome evaluation storage module 140, and output the determination result.

In summary, the physiological signal analysis method and the system thereof and the computer program product storing a physiological signal analysis program of the invention combine user opinions to perform analysis. The shortage that conventional physiological signal detection and analysis instruments usually violate human determination required by users in actual operation process may be improved. The analysis and determination results output by the invention are more reliable to both doctors and patients such that the practical value thereof is improved. In addition, the method that profession opinions of users and physiological data from subjects may be combined for analysis improves indeed accuracy of the system in detection and analysis to improve diagnosis and treatment work efficiency of doctors. Moreover, with the setting of data input threshold, the invention may reduce input of lots of unnecessary data, such that not only the system operation load of physiological signal detection and analysis instruments is reduced, but also the complexity of diagnosis done by doctors may be simplified.

The examples above are only illustrative to explain principles and effects of the invention, but not to limit the invention. It will be apparent to those skilled in the art that modifications and variations can be made without departing from the spirit and scope of the invention. Therefore, the protection range of the rights of the invention should be as defined by the appended claims.

What is claimed is:

1. A physiological signal analysis method, the method including steps of:
   collecting physiological signal from a subject through a heartbeat detecting device;
   retrieving characteristic values from said physiological signal for detection of a predetermined waveform and output of a detection result, wherein the detection result is saved in a memory;
   allowing user to enter syndrome evaluation data according to said detection result;
   generating syndrome recognition parameters and syndrome weight parameters by a processor according to said entered syndrome evaluation data for saving; and
   analyzing the physiological signal collected from the subject by the processor according to the saved syndrome recognition parameters, and outputting a determination result; the determination result is further selectively modified by the user and is saved in a memory of a syndrome evaluation database,
   wherein detection steps of said predetermined waveform includes steps of:
   defining peak detection intervals of the physiological signal, and setting threshold parameters of input data in said peak detection intervals, said threshold parameters being used for excluding unnecessary sampling points in said peak detection intervals;
   receiving said collected physiological signal input data until the collected physiological signal input data is determined to satisfy said set threshold of the input data in the peak detection intervals;
   obtaining peak data of the physiological signal in each of said peak detection intervals; and
   comparing waveform presence time corresponding to the peak data of two adjacent peak detection intervals to determine whether or not said two peak datum belong to the same physiological signal, and updating said set threshold parameters of the input data in the peak detection intervals according to said determination result, and obtaining peak presence time of said physiological signal.

2. The physiological signal analysis method as claim 1, wherein said physiological signal includes EEG, ECoG, EKG, EMG or ECG physiological signal.

3. The physiological signal analysis method as claim 1, wherein the steps of outputting the determination result output from the analysis for the physiological signal collected from the subject according to the saved syndrome recognition parameters and syndrome weight parameters include steps of:
   collecting the physiological signal from the subject in one peak detection interval according to said defined peak detection intervals, and executing wavelet transform process for the physiological signal collected in said peak detection intervals to generate wavelet coefficients;
   obtaining the peak presence time in said peak detection interval;
   dividing the peak detection interval in which said peak presence time is obtained into a plurality of small intervals, calculating a sum of differences between two curves of the wavelet coefficients and said saved syndrome recognition parameters in each of the small intervals; and
   grading each of said divided small intervals according to the calculated sum of the differences between said two curves, wherein process of said grading is based on syndrome grades corresponding to said syndrome recognition parameters, wherein said syndrome grade is one of the aforementioned syndrome weight parameters, and the syndrome grades of each of the small intervals are summed for analysis and output of said determination result.

4. The physiological signal analysis method as claim 3, wherein a small one calculated sum of the differences between the two curves of the wavelet coefficients in the small intervals and said saved syndrome recognition parameters indicates that the physiological signal from said subject is close to said saved syndrome recognition parameters, such that said syndrome grades can be graded.

5. The physiological signal analysis method as claim 4, wherein the steps of outputting the determination result output from the analysis for the physiological signal collected from the subject further include steps of:
   after the syndrome grades of said small intervals being graded because of the small sum of the differences between the two curves of the calculated wavelet coefficients in the small intervals and said saved syndrome recognition parameters, summing the syndrome grades of said syndrome recognition parameters of each of the small intervals, and determining the syndrome indicated by said peak detection intervals according to high syndrome grades corresponding to said syndrome recognition parameters.

6. The physiological signal analysis method as claim 5, further including steps of: setting parameter values for recording grading number, wherein said grading number is one of the aforementioned syndrome weight parameters, recording said grading number as the calculated sum of the differences between the two curves of the wavelet coefficients in the small intervals and said saved syndrome recognition parameters is a small one, and performing the step of summing the syndrome grades of each of said syndrome recognition parameters for each of the small intervals as said grading number reaches a predetermined value.

7. The physiological signal analysis method as claim 3, further including steps of: allowing the user to modify the entered syndrome evaluation data based on said determination result in order to optimize said saved syndrome recognition parameters and syndrome weight parameters.

8. A non-transitory tangible computer program product for storing physiological signal analysis program, wherein a physiological signal analysis method includes steps of:
   collecting physiological signal from a subject through a heartbeat detecting device;
   retrieving characteristic values from said physiological signal for detection of a predetermined waveform and output of a detection result, wherein the detection result is saved in a memory;
   allowing user to enter syndrome evaluation data according to said detection result;
   generating syndrome recognition parameters and syndrome weight parameters by a processor according to said entered syndrome evaluation data for saving; and
   analyzing the physiological signal collected from the subject by the processor according to the saved syndrome recognition parameters, and outputting a determination result; the determination result is further selectively modified by the user and is saved in a memory of a syndrome evaluation database, wherein detection steps of said predetermined waveform includes steps of:

defining peak detection intervals of the physiological signal, and setting threshold parameters of input data in said peak detection intervals, said threshold parameters being used for excluding unnecessary sampling points in said peak detection intervals;

receiving said collected physiological signal input data until the collected physiological signal input data is determined to satisfy said set threshold of the input data in the peak detection intervals;

obtaining peak data of the physiological signal in each of said peak detection intervals; and comparing waveform presence time corresponding to the peak data of two adjacent peak detection intervals to determine whether or not said two peak datum belong to the same physiological signal, and updating said set threshold parameters of the input data in the peak detection intervals according to said determination result, and obtaining peak presence time of said physiological signal.

9. A physiological signal analysis system for user to determine syndrome by a physiological signal from a subject, the system including:

a physiological signal detection module for retrieving characteristic values of the physiological signal collected from the subject in order for detection of a predetermined waveform and output of the detection result, wherein the detection result is saved in a memory;

a syndrome evaluation module for the user to determine the syndrome according to the detection result output by said physiological signal detection module, and to enter corresponding syndrome evaluation data for generating syndrome recognition parameters and syndrome weight parameters by a processor according to said entered syndrome evaluation data; and a determination module for analyzing the detection result output by said physiological signal detection module according to the syndrome recognition parameters and syndrome weight parameters generated by said syndrome evaluation module, and for outputting a determination result, the determination result is further selectively modified by the user and is saved in a memory of a syndrome evaluation database, wherein said physiological signal detection module includes:

a digital filter unit for filtering out noise in said collected physiological signal, and outputting a signal of a frequency band occupied by said retrieved physiological signal;

a wavelet transform unit for executing wavelet transform process for the signal output by said digital filter unit to generate wavelet coefficients in order to retrieve characteristic values in said physiological signal, and saving said generated wavelet coefficients in a storage unit; and a peak detection unit for performing waveform analysis and detection for the wavelet coefficients in said storage unit to obtain peak presence time of said physiological signal, and outputting said detection result, wherein said peak detection unit predefines the peak detection intervals of the physiological signal, and sets threshold parameters of input data in said peak detection intervals, said threshold parameters being used to exclude unnecessary sampling points in said peak detection intervals, and to receive the input data of said collected physiological signal until the input data of the collected physiological signal is determined to satisfy threshold of the input data in said set peak detection intervals; obtains peak data of the physiological signal in each of said peak detection intervals; compares waveform presence time corresponding to the peak data of two adjacent peak detection intervals in order to determine whether or not said two peak datum are both belong to the same physiological signal, and update the threshold parameters of the input data in said set peak detection intervals according to said determination result, and obtain the peak presence time of said physiological signal.

10. The physiological signal analysis system as claim 9, further including: a syndrome evaluation storage module for saving the syndrome recognition parameters generated by said syndrome evaluation module, said determination module collecting the physiological signal of the subject in one peak detection interval according to said defined peak detection interval, and obtaining the peak presence time in said peak detection interval and the wavelet coefficients corresponding to the physiological signal in said peak detection interval, dividing the peak detection interval of said obtained peak presence time into a plurality of small intervals, calculating sum of differences between two curves for the wavelet coefficients in each of the small intervals and said saved syndrome recognition parameters, grading each of said divided small intervals according to the sum of the differences between said calculated two curves, wherein said grading is processed according to syndrome grades corresponding to said syndrome recognition parameters, wherein said syndrome grade is one of the aforementioned syndrome weight parameters, and the syndrome grades of each of the small intervals are summed for analysis to result in and output said determination result.

11. The physiological signal analysis system as claim 10, wherein a small one calculated sum of the differences between the two curves of the wavelet coefficients in the small intervals and said saved syndrome recognition parameters indicates that the physiological signal from said subject is close to said saved syndrome recognition parameters, such that said syndrome grades can be graded.

12. The physiological signal analysis system as claim 10, wherein after the syndrome grades of said small intervals being graded because of the small sum of the differences between the two curves of the calculated wavelet coefficients in the small intervals and said saved syndrome recognition parameters by the determination module, summing the syndrome grades of said syndrome recognition parameters of each of the small intervals, and determining the syndrome indicated by said peak detection intervals according to high syndrome grades corresponding to said syndrome recognition parameters.

13. The physiological signal analysis system of claim 12, wherein said determination module further sets parameter values to record grading number, wherein said grading number is one of the aforementioned syndrome weight parameters, said grading number is recorded as the sum of the differences between the two curves for the calculated wavelet coefficients in the small intervals and the saved syndrome recognition parameters is small, and the syndrome grades of each of the syndrome recognition parameters for each of the small intervals are summed as said grading number reaches a predetermined value, such that the syndrome belonging to said peak detection interval is determined according to the high syndrome grades corresponding to the syndrome recognition parameters.

14. The physiological signal analysis system of claim 9, wherein said physiological signal detection module further includes a sensing unit for sensing physiological condition of said subject in order to obtain the physiological signal from said subject.

15. The physiological signal analysis system of claim 9, wherein said digital filter unit is low pass filter, high pass filter, band pass filter, notch filter, or the combination thereof.

16. The physiological signal analysis system of claim 9, further including: a syndrome evaluation storage module, and said syndrome evaluation module including:
- a wavelet inverse transform unit for executing wavelet inverse transform process for the wavelet coefficients output by said wavelet transform unit in order to restore an original physiological signal thereof;
- a syndrome evaluation unit for the user to determine syndrome from the detection result output by said peak detection unit, and to enter the corresponding syndrome evaluation data; and
- a conversion unit for generating the syndrome recognition parameters and syndrome weight parameters according to the syndrome evaluation data input from said syndrome evaluation unit, and for saving thereof in said syndrome evaluation storage module.

17. The physiological signal analysis system of claim 16, wherein said syndrome evaluation unit further allows the user to modify the syndrome evaluation data entered by the user according to said determination result to modify said determination result, and thereby optimizes the syndrome recognition parameters and syndrome weight parameters saved in said syndrome evaluation storage module.

* * * * *